_United States Patent_ [19]

Lesher et al.

[11] Patent Number: 4,469,699

[45] Date of Patent: Sep. 4, 1984

[54] 5-(4-THIAZOLYL)-6-ALKYL-2(1H)-PYRIDINONES AND THEIR CARDIOTONIC USE

[75] Inventors: George Y. Lesher, Schodack; Baldev Singh, East Greenbush, both of N.Y.

[73] Assignee: Sterling Drug Inc., New York, N.Y.

[21] Appl. No.: 411,558

[22] Filed: Aug. 25, 1982

[51] Int. Cl.$^3$ .................... C07D 417/04; A61K 31/44
[52] U.S. Cl. ................................... 424/263; 546/280; 546/288
[58] Field of Search .......................... 546/280; 424/263

[56]  References Cited

U.S. PATENT DOCUMENTS

| | | | |
|---|---|---|---|
| 4,004,012 | 1/1977 | Lesher et al. | 424/263 |
| 4,072,746 | 2/1978 | Lesher et al. | 424/263 |
| 4,276,293 | 6/1981 | Lesher et al. | 424/248.4 |
| 4,312,875 | 1/1982 | Lesher et al. | 424/266 |
| 4,313,951 | 2/1982 | Lesher et al. | 424/263 |

OTHER PUBLICATIONS

Ariesan et al., Chemical Abstracts, vol. 74, No. 23, Abst. No. 125,358g, Jun. 7, 1971.

_Primary Examiner_—Alan L. Rotman
_Attorney, Agent, or Firm_—Robert K. Bair; B. Woodrow Wyatt; Paul E. Dupont

[57]  ABSTRACT

3-Q-4-$R_2$-5-(2-Q'-5-$R_3$-4-thiazolyl)-6-$R_1$-2(1H)-pyridinones (I), where $R_1$ is alkyl having from one to four carbon atoms, $R_2$ is hydrogen or methyl, $R_3$ is hydrogen or alkyl having from one to three carbon atoms, Q is amino, carbamyl, carboxy, cyano or hydrogen, and Q' is alkyl having from one to four carbon atoms, amino or $R_4$NH where $R_4$ is alkyl having from one to four carbon atoms, or acid-addition salts thereof where at least one of Q and Q' is amino or Q' is $R_4$NH, are useful as cardiotonics (I where Q is amino, cyano or hydrogen) and/or as intermediates (I where Q is cyano, carbamyl or carboxy). Also shown as intermediates are 1,2-dihydro-4-$R_2$-5-[$R_3$CH(Br)CO]-6-$R_1$-2-oxo-3-pyridinecarbonitriles (II), and, also, processes for preparing I and II.

9 Claims, No Drawings

5-(4-THIAZOLYL)-6-ALKYL-2(1H)-PYRIDINONES AND THEIR CARDIOTONIC USE

CROSS-REFERENCE TO RELATED APPLICATION

Lesher and Singh copending U.S. patent application Ser. No. 357,872, filed Mar. 15, 1982 now U.S. Pat. No. 4,412,077, issued Oct. 25, 1983, discloses and claims the preparation of compounds disclosed herein as intermediates, namely, 1,2-dihydro-4-$R_2$-5-(lower-alkanoyl)-6-(lower-alkyl)-2-oxo-3-pyridinecarbonitriles, where $R_2$ is hydrogen or methyl.

BACKGROUND OF THE INVENTION

1. Field of the Invention

This invention relates to thiazolylpyridinones, their preparation and their use as cardiotonics.

2. Description of the Prior Art

Lesher and Opalka [U.S. Pat. Nos. 4,004,012, issued Jan. 18, 1977, and 4,072,746, issued Feb. 7, 1978] show as cardiotonic agents 3-amino(or cyano)-5-(pyridinyl)-2(1H)-pyridinones. A preferred embodiment of these compounds is 3-amino-5-(4-pyridinyl)-2(1H)-pyridinone, now generically known as amrinone and alternatively named 5-amino-[3,4'-bipyridin]-6(1H)-one. Various methods are shown for preparing the 3-cyano-5-(pyridinyl)-2(1H)-pyridinones, alternatively named 1,2-dihydro-2-oxo-5-(pyridinyl)nicotinonitriles, for example, by reacting α-(pyridinyl)-β-(dialkylamino)acrolein with α-cyanoacetamide and the conversion of said substituted-nicotinonitriles to the corresponding substituted-nicotinamides and substituted-nicotinic acids. U.S. Pat. No. 4,072,746 also shows, inter alia, 3-Q-5-(pyridinyl)-2(1H)-pyridinones where Q is hydrogen by decarboxylating the corresponding compound where Q is carboxy. The disclosure of U.S. Pat. No. 4,072,746 also is shown in Lesher and Opalka U.S. Pat. Nos. 4,107,315, 4,137,233, 4,199,586 and 4,225,715.

Lesher, Opalka and Page U.S. Pat. No. 4,276,293, issued June 30, 1981, shows inter alia 1,2-dihydro-6-(lower-alkyl)-2-oxo-5-(pyridinyl)nicotinonitriles by reacting a 1-(pyridinyl)-2-(dimethylamino)ethenyl lower-alkyl ketone with α-cyanoacetamide and the conversion, by hydrolysis and decarboxylation, of said nicotinonitriles to the corresponding 6-(lower-alkyl)-5-(pyridinyl)-2(1H)-pyridinones.

Lesher and Philion U.S. Pat. No. 4,313,951, issued Feb. 2, 1982 from Application Ser. No. 198,461, filed Oct. 20, 1980 as a continuation-in-part of application Ser. No. 97,504, filed Nov. 26, 1979 and now abandoned, discloses and claims as cardiotonics, inter alia, 1,2-dihydro-6-(lower-alkyl)-2-oxo-5-(pyridinyl)-nicotinonitriles and their preparation, and also the conversion by hydrolysis of said nicotinonitriles to the corresponding nicotinamides and subsequent conversion of the latter to the corresponding 3-amino-6-(lower-alkyl)-5-(pyridinyl)-2(1H)-pyridinones.

Lesher, Opalka and Page U.S. Pat. No. 4,312,875, issued Jan. 26, 1982 from Application Ser. No. 204,726, filed Nov. 6, 1980 as a continuation-in-part of U.S. application Ser. No. 135,100, filed Mar. 28, 1980 and now U.S. Pat. No. 4,297,360, issued Oct. 27, 1981, discloses and claims as cardiotonics, 6-(lower-alkyl)-5-(pyridinyl)-2(1H)-pyridinones.

3. Prior Publications

The following publications appeared prior to the filing of the instant application but subsequent to completion of applicants' invention disclosed and claimed herein: Sandoz AG U.K. Patent Application No. 2,070,606, published Sept. 9, 1981, and corresponding Belgian Patent No. 887,737, published Sept. 2, 1981, which disclose, inter alia, as cardiotonic agents and claim selected 3-amino-6-$R_2$-5-aryl-2(1H)-pyridinones where $R_2$ is hydrogen or lower-alkyl and aryl is, inter alia, 4-thiazolyl. These compounds are reportedly prepared from the corresponding 1,2-dihydro-2-oxo-6-$R_2$-5-arylnicotinamides, in turn, prepared from the corresponding 1,2-dihydro-2-oxo-6-$R_2$-5-arylnicotinonitriles, in turn, prepared by reacting cyanoacetamide with 4-dimethylamino-3-aryl-3-buten-2-one.

SUMMARY OF THE INVENTION

In a composition of matter aspect, the invention resides in 3-Q-4-$R_2$-5-(2-Q'-5-$R_3$-4-thiazolyl)-6-$R_1$-2(1H)-pyridinones (I), useful as cardiotonic agents, where Q, Q', $R_1$, $R_2$ and $R_3$ are defined hereinbelow.

A composition aspect of the invention resides in the cardiotonic composition for increasing cardiac contractility, said composition comprising a pharmaceutically acceptable carrier, and as the active component thereof, a cardiotonically effective amount of 3-Q-4-$R_2$-5-(2-Q'-5-$R_3$-4-thiazolyl)-6-$R_1$-2(1H)-pyridinone (I), where Q is amino, cyano or hydrogen.

A method aspect of the invention resides in the method for increasing cardiac contractility in a patient requiring such treatment which comprises administering to said patent a medicament comprising a pharmaceutically acceptable carrier and, as the active component, a cardiotonically effective amount of 3-Q-4-$R_2$-5-(2-Q'-5-$R_3$-4-thiazolyl)-6-$R_1$-2(1H)-pyridinone (I) where Q is amino, cyano or hydrogen.

The invention in its process aspects comprises: (a) the process for preparing 1,2-dihyro-4-$R_2$-5-[2-bromo-(lower-alkanoyl)]-6-$R_1$-2-oxo-3-pyridinecarbonitrile (II) by reacting a 3-Q-4-$R_2$-5-(lower-alkanoyl)-6-$R_1$-2(1H)-pyridinone with bromine; (b) the process for preparing 1,2-dihydro-4-$R_2$-5-(2-Q'-5-$R_3$-4-thiazolyl)-6-$R_1$-2-oxo-3-pyridinecarbonitrile (I, Q is cyano and Q' is alkyl having one to three carbon atoms or Q' is $R_4NH$) by reacting II with a lower-alkanethioamide or by reacting II with N-$R_4$-thiourea; (c) the process for producing 4-$R_2$-5-(2-Q'-5-$R_3$-4-thiazolyl)-6-$R_1$-2(1H)-pyridinone (I, Q is hydrogen) by first hydrolyzing 1,2-dihydro-4-$R_2$-5-(2-Q'-5-$R_3$ -4-thiazolyl)-6-$R_1$-2-oxo-3-pyridinecarbonitrile (I, Q is cyano) to produce the corresponding -3-pyridinecarboxylic acid (I, Q is carboxy) and then decarboxylating the -3-pyridinecarboxylic acid; and, (d) the process for preparing 3-amino-4-$R_2$-5-(2-Q'-5-$R_3$-4-thiazolyl)-6-$R_1$-2(1H)-pyridinone (I, Q is amino) by first hydrolyzing 1,2-dihydro-4-$R_2$-5-(2-Q'-5-$R_3$-4-thiazolyl)-6-$R_1$-2-oxo-3-pyridinecarbonitrile (I, Q is cyano) to produce the corresponding -3-pyridinecarboxamide (I, Q is carbamyl) and then converting said -3-pyridinecarboxamide (I, Q is carbamyl) to the corresponding 3-amino compound (I, Q is amino).

Another composition aspect of the invention resides in 1,2-dihydro-4-$R_2$-5-[2-bromo-(lower-alkanoyl)]-6-$R_1$-2-oxo-3-pyridinecarbonitrile (II), useful as an intermediate.

DETAILED DESCRIPTION INCLUSIVE OF PREFERRED EMBODIMENTS

A composition of matter aspect of the invention resides in a 3-Q-4-$R_2$-5-2(2-Q'-5-$R_3$-4-thiazolyl)-6-$R_1$-2(1H)-pyridinone having formula I

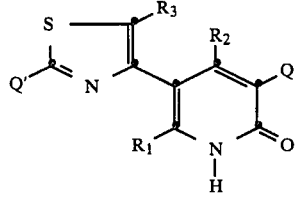

where $R_1$ is alkyl having from one to four carbon atoms, $R_2$ is hydrogen or methyl, $R_3$ is hydrogen or alkyl having from one to three carbon atoms, Q is amino, carbamyl, carboxy, cyano or hydrogen, and Q' is alkyl having from one to four carbon atoms, amino or $R_4NH$ where $R_4$ is alkyl having from one to four carbon atoms, or an acid-addition salt thereof where at least one of Q and Q' is amino or Q' is $R_4NH$. The compounds of formula I where Q is amino, cyano or hydrogen are useful as cardiotonics, as determined by standard pharmacological evaluation procedures. The compounds of formula I where Q is carbamyl, carboxy or cyano are useful as intermediates for preparing the cardiotonics of formula I where Q is amino or hydrogen. Preferred embodiments are those of formula I where Q is cyano, $R_1$ is methyl or ethyl, and $R_2$ and $R_3$ are each hydrogen. A particularly preferred embodiment is 1,2-dihydro-6-methyl-5-(2-methyl-4-thiazolyl)-2-oxo-3-pyridinecarbonitrile (I, Q is cyano, Q' and $R_1$ are each methyl, and $R_2$ and $R_3$ are each hydrogen.

A composition aspect of the invention resides in a cardiotonic composition for increasing cardiac contractility, said composition comprising a pharmaceutically acceptable carrier and, as the active component thereof, a cardiotonically effective amount of the compound of formula I where $R_1$, $R_2$, $R_3$ and Q' are as defined above in formula I and Q is amino, cyano or hydrogen; or pharmaceutically acceptable acid-addition salt thereof where at least one of Q and Q' is amino or Q' is $R_4NH$. Preferred embodiments of this composition aspect of the invention are those where the active component is the compound of formula I where Q is cyano, $R_1$ is methyl or ethyl, and $R_2$ and $R_3$ are each hydrogen. A particularly preferred embodiment is the composition where the active component is 1,2-dihydro-6-methyl-5-(2-methyl-4-thiazolyl)-2-oxo-3-pyridinecarbonitrile.

A method aspect of the invention resides in the method for increasing cardiac contractility in a patient requiring such treatment which comprises administering orally or parenterally in a solid or liquid dosage form to such patient a composition comprising a pharmaceutically acceptable carrier and, as active component thereof, a cardiotonically effective amount of the compound of formula I where $R_1$, $R_2$, $R_3$ and Q' are as defined above in formula I and Q is amino, cyano or hydrogen, or pharmaceutically acceptable salt thereof where at least one of Q and Q' is amino or Q' is $R_4NH$. Preferred and particularly preferred embodiments of this method aspect of the invention are those where the active component is the same as the active component of the respective preferred and particularly preferred composition embodiments described in the immediately preceding paragraph.

Another composition of matter aspect of the invention resides in 1,2-dihydro-4-$R_2$-5-[$R_3CH(Br)CO$]-6-$R_1$-2-oxo-3-pyridinecarbonitrile having formula II

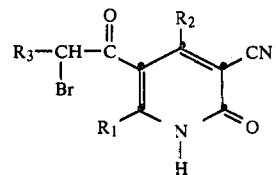

where $R_1$, $R_2$ and $R_3$ have the meanings given for formula I. The compounds of formula II are useful as intermediates for preparing the compounds of formula I where Q is cyano. Preferred embodiments are the compounds of formula II where $R_1$ is methyl or ethyl, and $R_2$ and $R_3$ are each hydrogen.

A process aspect of the invention resides in the process which comprises reacting 1,2-dihydro-4-$R_2$-5-($R_3CH_2CO$)-6-$R_1$-2-oxo-3-pyridinecarbonitrile with bromine to produce 1,2-dihydro-4-$R_2$-5-[$R_3CH(Br)CO$]-6-$R_1$-2-oxo-3-pyridinecarbonitrile of formula II, where $R_1$, $R_2$ and $R_3$ have the meanings given for formula I.

Another process aspect of the invention resides in the process which comprises reacting the compound of formula II with a compound of the formula Q'-C(=S)$NH_2$ to produce the compound of formula I where Q is cyano and $R_1$, $R_2$, $R_3$ and Q' have the meanings given for formula I.

Another process aspect of the invention resides in the process which comprises successively converting 1,2-dihydro-4-$R_2$-5-(2-Q'-5-$R_3$-4-thiazolyl)-6-$R_1$-2-oxo-3-pyridinecarbonitrile of formula I where Q is cyano to the corresponding 3-carboxy and 3-unsubstituted compounds by respectively hydrolyzing the 3-cyano compound to produce the 3-carboxy compound and decarboxylating the 3-carboxy compound, where $R_1$, $R_2$, $R_3$ and Q' have the meanings of formula I.

Another process aspect of the invention resides in the process which comprises successively converting 1,2-dihyro-4-$R_2$-5-(2-Q'-5-$R_3$-4-thiazolyl)-6-$R_1$-2-oxo-3-pyridinecarbonitrile of formula I where Q is cyano to the corresponding 3-carbamyl (Q is carbamyl) and 3-amino (Q is amino) compounds by respectively hydrolyzing the 3-cyano compound to produce the 3-carbamyl compound and reacting the 3-carbamyl compound with a reagent capable of converting carbamyl to amino.

The various alkyl radicals having one to three or one to four carbon atoms, e.g., one of the meanings for Q' or the meaning for $R_1$ or $R_3$ can have the carbon atoms arranged as straight or branched chains, illustrated by methyl, ethyl, n-propyl, isopropyl, n-butyl, sec.-butyl, tert.-butyl and isobutyl.

The compounds of the invention having formula I in which at least one of Q and Q' is amino or Q' is $R_4NH$ are useful both in the free base and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base form of the cardiotonically active compounds of the invention are not vitiated by side effects ascribable to the anions. In practicing the invention, it is convenient to use the free base form; however, appropriate pharmaceutically acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds of the invention were assigned on the basis of evidence provided by infrared, nuclear magnetic resonance and mass spectra, and by the correspondence of calculated and found values for the elemental analyses.

The manner of making and using the instant invention will now be generally described so as to enable a person skilled in the art of pharmaceutical chemistry to make and use the same.

The reaction of 1,2-dihydro-4-$R_2$-5-($R_3CH_2CO$)-6-$R_1$-2-oxo-3-pyridinecarbonitrile with bromine to produce 1,2-dihydro-4-$R_2$-5-[$R_3CH(Br)CO$]-6-$R_1$-2-oxo-3-pyridinecarbonitrile (II) is carried out by mixing the reactants at about 25° C. to 65° C., preferably at about 60° C. to 65° C., in an inert solvent such as chloroform.

The intermediate 1,2-dihydro-4-$R_2$-5-($R_3CH_2CO$)-6-$R_1$-2-oxo-3-pyridinecarbonitriles, which are disclosed as intermediates and claimed as cardiotonics in said copending application Ser. No. 357,872, filed Mar. 15, 1982, are prepared by a generally known method [Sumthankar et al., Indian J. of Chemistry 11, 1315-16 (1973)] or an improved modification thereof, as illustrated hereinbelow in the specific exemplary disclosure.

The reaction of 1,2-dihydro-4-$R_2$-5-[$R_3CH(Br)CO$]-6-$R_1$-2-oxo-3-pyridinecarbonitrile (II) with Q'-C(=S)$NH_2$ to produce 1,2-dihydro-4-$R_2$-5-(2-Q'-5-$R_3$-4-thiazolyl)-6-$R_1$-2-oxo-3-pyridinecarbonitrile (I, Q is cyano) is conveniently carried out by heating the reactants at about 70° C. to 95° C., preferably about 85° C. to 95° C., in an inert solvent, preferably dimethylformamide. Other solvents that can be used include tetramethyl urea, p-dioxane and acetonitrile.

The 1,2-dihydro-4-$R_2$-5-(2-Q'-5-$R_3$-4-thiazolyl)-6-$R_1$-2-oxo-3-pyridinecarbonitriles (I, Q is cyano) are conveniently hydrolyzed to produce the corresponding substituted 3-pyridinecarboxylic acids under aqueous acidic conditions by heating with aqueous mineral acid, preferably sulfuric acid and preferably at about 70° C. to 130° C. Optionally, aqueous phosphoric, hydrochloric, hydrobromic or other acids can be used. Alternatively, this hydrolysis can be carried out under aqueous alkaline conditions, preferably using aqueous sodium or potassium hydroxide at about 95°–100° C.

The partial hydrolysis of I where Q is cyano to produce I where Q is carbamyl is carried out preferably using concentrated sulfuric acid at room temperature, i.e., about 20° C. to 30° C. Optionally, other strong inorganic acids, e.g., phosphoric acid, polyphosphoric acid, can be used in place of sulfuric acid.

Decarboxylation of I where Q is carboxy to produce I where Q is hydrogen is carried out by heating the carboxy compound at about 250° to 300° C. in a suitable solvent, for example, diethyl phthalate, eutectic mixture of diphenyl and diphenyl ether (DOWTHERM® A), mineral oil, and the like. Alternatively, I where Q is cyano can be conveniently converted to I where Q is hydrogen in boiling 85% sulfuric acid.

The conversion of I where Q is carbamyl to produce I where Q is amino is carried out by reacting the carbamyl compound with a reagent capable of converting carbamyl to amino. The reaction is conveniently run by mixing I where Q is carbamyl in aqueous mixture with an alkali metal hypohalite, preferably hypobromite or hypochlorite, initially in an ice bath and then at room temperature and then acidifying the reaction mixture, preferably with an aqueous mineral acid, e.g., hydrochloric acid. The reaction is conveniently run by adding bromine to a stirred ice cold aqueous solution containing I where Q is carbamyl and sodium or potassium hydroxide to form the hypobromite in situ, stirring the reactants in an ice bath and then allowing the reaction to warm up to room temperature.

The following examples will further illustrate the invention without, however, limiting it thereto.

A.
1,2-DIHYDRO-4-$R_2$-5-($R_3CH_2CO$)-6-$R_1$2-OXO-3-PYRIDINE CARBONITRILES

A-1. 5-Acetyl-1,2-dihydro-6-methyl-2-oxo-3-pyridinecarbonitrile—A solution containing 60 g of dimethylformamide dimethyl acetal and 50 g of 2,4-pentanedione was heated on a steam bath for 2.5 hours and cooled. To the resulting solution containing 3-dimethylaminomethylene-2,4-pentanedione was added 300 ml of methanol, 27 g of sodium methoxide and 47 g of cyanoacetamide. The resulting mixture was heated on a steam bath for 4 hours, the hot solution poured into 700 ml of water, and the aqueous mixture acidified with acetic acid and chilled in an ice bath. The solid that separated was collected, dried, and heated with 400 ml. of methanol. Insoluble material was filtered from the hot methanol mixture and the filtrate cooled. The product that separated was collected and dried at 90° C. to produce 24.6 g of 5-acetyl-1,2-dihydro-6-methyl-2-oxo-3-pyridinecarbonitrile, m.p. 227°–230° C. [Sunthankar et al., supra, m.p. 231° C.]

A-2. 1,2-Dihydro-6-methyl-2-oxo-5-(n-propanoyl)-3-pyridinecarbonitrile and 5-acetyl-6-ethyl-1,2-dihydro-2- oxo-3-pyridinecarbonitrile—A mixture containing 34 g of 2,4-hexanedione, 50 ml of dimethylformamide and 40 ml of dimethylformamide dimethyl acetal was allowed to stand at room temperature overnight and then concentrated on a rotary evaporator at steam bath temperature to yield, as a liquid, 3-dimethylaminomethylene-2,4-hexanedione. A mixture containing said 3-dimethylaminomethylene-2,4-hexanedione, 300 ml of methanol 25.2 g of cyanoacetamide and 16.2 g of sodium methoxide was refluxed with stirring for 3 hours and then concentrated in vacuo to remove the methanol. The residue was dissolved in 300 ml of warm water and filtered. The filtrate was acidified with acetic acid and the resulting precipitate was collected, washed with water, dried in vacuo at 90°–95° C. and recrystallized from dimethylformamide (75 ml) to yield 7.8 g of 1,2-dihydro-6-methyl-2-oxo-5-(n-propanoyl)-3-pyridinecarbonitrile, m.p. 265°–268° C. with decomposition. The mother liquor was concentrated to dryness and digested with hot methanol and cooled. The separated solid was dried, 20.2 g, and recrystallized from dimethylformamide to yield 9.8 g of finely crystalline material, m.p. 259°–263° C. with decomposition. The NMR spectral data for this compound indicated it to be mostly said 1,2-dihydro-6-methyl-2-oxo-5-(n-propanoyl)-3-pyridinecarbonitrile. The resulting mother liquors were combined and concentrated on a rotary evaporator and the resulting residue was recrystallized from ethanol to yield 20.4 g of solid, m.p. 220°–226° C. The NMR spectral data for this solid indicated it to be a 5:4 mixture of said 1,2-dihydro-6-methyl-2-oxo-5-(n-propanoyl)-3-pyridinecarbonitrile and 5-acetyl-6-ethyl-1,2-dihydro-2-oxo-3-pyridinecarbonitrile. Although preliminary attempts to separate the two compounds by fractional crystallization were unsuccessful, it is contemplated that the two compounds would be separable by other conventional separation techniques, e.g., chromatography.

A-3. 5-Acetyl-1,2-dihydro-6-methyl-2-oxo-3-pyridinecarbonitrile and 5-acetyl-1,2-dihydro-6-methyl-2-oxo-3-pyridinecarboxamide—A mixture containing 200 g of 2,4-pentanedione and 300 ml of dimethylformamide dimethyl acetal was heated under reflux on a steam bath for 5 hours and then allowed to stand at room temperature overnight. The excess solvent was distilled off using a rotary evaporator to a constant weight of 307 g, as an oil, of 3-dimethylaminomethylene-2,4-pentanedione which was combined with 700 ml of methanol and 168 g of cyanoacetamide followed by 108 g of sodium methoxide with stirring and cooling. The reaction mixture was heated under reflux for 7 hours, cooled and treated with 150 ml of glacial acetic acid. The separated solid was collected and the filtrate evaporated to dryness. The residue was treated with 700 ml of water and the insoluble material was collected, washed with water and dried. The two solids were combined and refluxed with 1 liter of methanol. The insoluble beige solid was collected, washed with hot methanol and dried in vacuo at 90°–95° C. to yield 55.8 g of 5-acetyl-1,2-dihydro-6-methyl-2-oxo-3-pyridine-carboxamide, m.p. >320° C. Both filtrates were concentrated to a volume of about 800 ml and cooled. The separated solid was collected and dried in vacuo at 90°–95° C. to yield 100 g of 5-acetyl-1,2-dihydro-6-methyl-2-oxo-3-pyridinecarbonitrile, m.p. 226°–229° C. Further concentration of the mother liquors yielded another 44.2 g of 5-acetyl-1,2-dihydro-6-methyl-2-oxo-3-pyridinecarbonitrile, m.p. 221°–225° C.

A-4. 5-Acetyl-1,2-dihydro-4,6-dimethyl-2-oxo-3-pyridinecarbonitrile—It is contemplated that this compound can be obtained following the procedure described in Example A-1 using in place of dimethylformamide dimethyl acetal a molar equivalent quantity of dimethylacetamide dimethyl acetal.

A-5. 6-Ethyl-1,2-dihydro-2-oxo-5-(n-propanoyl)-3-pyridinecarbonitrile—To a stirred mixture containing 200 ml of dimethylformamide and 128 g of 3,5-heptanedione was added 134 ml of dimethylformamide dimethyl acetal over a 15 minute period and the resulting mixture was allowed to stand at room temperature overnight. The reaction mixture was then heated on a steam bath for 1 hour and concentrated on a rotary evaporator to a constant weight of 186.4 g, as a deep yellow oil, of dimethylaminomethylene-3,5-hexanedione. To a stirred mixture containing 186.4 g of 4-dimethylaminomethylene-3,5-hexanedione, 92 g of cyanoacetamide and 1200 ml of methanol was added over a ten minute period 57 g of sodium methoxide, whereupon a mild exothermic reaction took place. The resulting mixture was refluxed for 2.5 hours, cooled and the methanol evaporated using a rotary evaporator. To the yellow residue was added 1 liter of water and 80 ml of glacial acetic acid. The separated white solid was collected, washed with water and dried in a vacuum oven at 90°–95° C. to yield 161 g of 6-ethyl-1,2-dihydro-2-oxo-5-(n-propanoyl)-3-pyridinecarbonitrile, m.p. 243°–245° C. This sample was used in the subsequent hydrolysis step described in Example B-2 to produce the corresponding nicotinic acid derivative. A 12 g sample of the -3-pyridinecarbonitrile was recrystallized from ethanol in quantitative yield to give the compound, as fine white needles, m.p. 245°–246° C.

A-6. 5-(n-Butanoyl)-1,2-dihydro-2-oxo-6-n-propyl-3-pyridinecarbonitrile, m.p. 205°–207° C., 25.4 g, was prepared following the procedure described in Example A-2 first using 25 g of 4,6-nonanedione, 25 ml of dimethylformamide dimethylacetal and 25 ml of dimethylformamide to yield, as an oil, 41 g of 5-(dimethylaminomethylene-4,6-nonanedionedione and then refluxing said dione with a mixture containing 14.3 g of cyanoacetamide, 300 ml of methanol and 9.3 g of sodium methoxide, evaporating the reaction mixture to dryness, dissolving the residue in 200 ml of water, acidifying with acetic acid, collecting and drying the product, and recrystallizing the 30.4 g of product from isopropyl alcohol.

B.
1,2-DIHYDRO-4-$R_2$-5-[$R_3$CH(BROMO)CO]-6-$R_1$-2-OXO-3-PYRIDINECARBONITRILES

B-1. 5-(Bromoacetyl)-1,2-dihydro-6-methyl-2-oxo-3-pyridinecarbonitrile—To a stirred mixture containing 66 g of 5-acetyl-1,2-dihydro-6-methyl-2-oxo-3-pyridinecarbonitrile and 450 ml of chloroform was added dropwise over a period of about 40 minutes a solution containing 60.8 g of bromine in 50 ml of chloroform. The resulting mixture was stirred at room temperature for about 3 hours and then heated on a steam bath for 30 minutes during which time the red color of the reaction mixture disappeared. The reaction mixture was allowed to stir at room temperature for 1 hour and then filtered using a sintered glass funnel. The filtered product was washed with acetone and dried at 60° C. to yield 97.8 g of 5-(bromoacetyl)-1,2-dihyro-6-methyl-2-oxo-3-pyridinecarbonitrile, m.p. 212°–214° C. with decomposition. A 20 g portion of this product was dissolved in a boiling mixture of 400 ml of methanol and 200 ml of dimethylformamide, the hot solution treated with decolorizing charcoal and filtered and the filtrate concentrated on a rotary evaporator to remove the solvents. The residue was boiled with methanol and the white powdery solid was collected, washed with methanol and dried to yield 16.4 g of 5-(bromoacetyl)-1,2-dihydro-6-methyl-2-oxo-3-pyridinecarbonitrile, m.p. 213°–215° C. with decomposition.

Following the procedure described in Example B-1 using in place of 5-acetyl-1,2-dihydro-6-methyl-2-oxo-3-pyridinecarbonitrile a molar equivalent quantity of the appropriate 1,2-dihydro-4-$R_2$-5-($R_3CH_2CO$)-6-$R_1$-2-oxo-3-pyridinecarbonitrile, it is contemplated that the corresponding 1,2-dihydro-4-$R_2$-5-[$R_3$-CH(Br)CO]-6-$R_1$-2-oxo--pyridinecarbonitriles of Examples B-2 thru B-6 can be obtained.

B-2. 5-(2-Bromo-n-propanoyl)-1,2-dihydro-6-methyl-3-oxo-3-pyridinecarbonitrile, using 1,2-dihydro-6-methyl-2-oxo-5-(n-propanoyl)-3-pyridinecarbonitrile.

B-3. 5-(Bromoacetyl)-6-ethyl-1,2-dihydro-2-oxo-3-pyridinecarbonitrile, using 5-acetyl-6-ethyl-1,2-dihydro-2-oxo-5-pyridinecarbonitrile.

B-4. 5-(Bromoacetyl)-1,2-dihydro-4,6-dimethyl-2-oxo-3-pyridinecarbonitrile, using 5-acetyl-1,2-dihydro-4,6-dimethyl-2-oxo-3-pyridinecarbonitrile.

B-5. 5-(2-Bromo-n-propanoyl)-6-ethyl-1,2-dihydro-2-oxo-3-pvridinecarbonitrile, using 6-ethyl-1,2-dihydro-2-oxo-5-(n-propanoyl)-3-pyridinecarbonitrile.

B-6. 5-(2-Bromo-n-butanoyl)-1,2-dihydro-2-oxo-6-n-propyl-3-pyridinecarbonitrile, using 5-(n-butanoyl)-1,2-dihydro-2-oxo-6-n-propyl-3-pyridinecarbonitrile.

C.
3-Q-4-$R_2$-5-(2-Q'-5-$R_3$-4-THIAZOLYL)-6-$R_1$-2(1H)-PYRIDINONES

C-1. 1,2-Dihydro-6-methyl-5-(2-methyl-4-thiazolyl)-2-oxo-3-pyridinecarbonitrile—A mixture containing 25.4 g of 5-(bromoacetyl)-1,2-dihydro-6-methyl-2-oxo-3-pyridinecarbonitrile, 7.5 g of thioacetamide and 100 ml of dimethylformamide was heated with stirring on a steam bath for 5 hours and then concentrated on a rotary evaporator. To the residual material was added 100 ml of water and 10 ml of concentrated aqueous ammonium hydroxide. The resulting mixture was filtered and the filtrate reacidified by adding acetic acid. The solid that separated was collected, washed with water and dried, and then recrystallized from dimethylformamide to produce 8.8 g of 1,2-dihydro-6-methyl-5-(2-methyl-4-thiazolyl)-2-oxo-3-pyridinecarbonitrile, m.p. 305°–307° C. with decomposition.

C-2. 5-(2-Amino-4-thiazolyl)-1,2-dihydro-6-methyl-2-oxo-3-pyridinecarbonitrile—A mixture containing 25.4 g of 5-bromoacetyl-1,2-dihydro-6-methyl-2-oxo-3-pyridinecarbonitrile, 7.9 g of thiourea and 100 ml of dimethylformamide was heated on a steam bath for 3 hours and then evaporated to dryness. The residual material was diluted with 100 ml of water followed by the addition of 10 ml of concentrated aqueous ammonium hydroxide. The resulting mixture was reacidified with acetic acid and the solid that separated was collected, washed with water and dried. The solid (15.8 g) was suspended in 400 ml of water and the mixture treated with 25 ml of concentrated ammonium hydroxide. The resulting mixture was stirred for 30 minutes and a small quantity of insoluble material was filtered off. The filtrate was concentrated on a rotary evaporator to a volume of about 200 ml and allowed to cool to room temperature. The crystalline precipitate was collected, washed with distilled water and dried in a vacuum oven at 90° C. to produce 7.3 g of 5-(2-amino-4-thiazolyl)-1,2-dihydro-6-methyl-2-oxo-3-pyridinecarbonitrile, m.p. 294°–296° C. with decomposition.

Acid-addition salts of 5-(2-amino-4-thiazolyl)-1,2-dihydro-6-methyl-2-oxo-3-pyridinecarbonitrile are conveniently prepared by adding to a mixture of 1 g of 5-(2-amino-4-thiazolyl)-1,2-dihydro-6-methyl-2-oxo-3-pyridinecarbonitrile in about 20 ml of aqueous methanol the appropriate acid, e.g., hydrochloric acid, methanesulfonic acid, concentrated sulfuric acid, concentrated phosphoric acid, to a pH of about 2 to 3, chilling the mixture after partially evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 5-(2-amino-4-thiazolyl)-1,2-dihydro-6-methyl-2-oxo-3-pyridinecarbonitrile and the appropriate acid, e.g., lactic acid or hydrochloric acid, to prepare respectively the lactate or hydrochloride salt of 5-(2-amino-4-thiazolyl)-1,2-dihydro-6-methyl-2-oxo-3-pyridinecarbonitrile in aqueous solution.

C-3. 1,2-Dihydro-6-methyl-5-(2-methyl-4-thiazolyl)-2-oxo-3-pyridinecarboxamide—To an ice cold stirred 150 ml portion of concentrated sulfuric acid was added over a 5 minute period 64.2 g of finely powdered 1,2-dihydro-6-methyl-5-(2-methyl-4-thiazolyl)-2-oxo-3-pyridinecarbonitrile and the resulting mixture was stirred in an ice bath for 30 minutes and then allowed to stand at room temperature overnight. The reaction mixture was poured onto ice (800 ml beaker half filled) and then neutralized by adding aqueous ammonium hydroxide solution. The tan solid that separated was collected, washed with water, recrystallized from dimethylformamide and dried in an oven at 90° C. for 2 days to produce 59.2 g of 1,2-dihydro-6-methyl-5-(2-methyl-4-thiazolyl)-2-oxo-3-pyridinecarboxamide, m.p. >300° C. with decomposition.

C-4. 1,2-Dihydro-6-methyl-5-(2-methyl-4-thiazolyl)-2-oxo-3-pyridinecarboxylic acid—A mixture containing 32 g of 1,2-dihydro-6-methyl-5-(2-methyl-4-thiazolyl)-2-oxo-3-pyridinecarboxamide, 50 ml of 35% aqueous sodium hydroxide solution and 300 ml of water was heated on a steam bath for 15 hours and cooled. The reaction mixture was filtered to remove a small quantity of insoluble material and the filtrate was acidified with concentrated hydrochloric acid. The resulting precipitate was collected, washed with water and dried in an oven at 80° C. to produce 30.2 g of 1,2-dihydro-6-methyl-5-(2-methyl-4-thiazolyl)-2-oxo-3-pyridinecarboxylic acid, m.p. 297°–299° C. with decomposition.

C-5. 6-Methyl-5-(2-methyl-4-thiazolyl)-2(1H)-pyridinone—To a 100 ml portion of boiling diethyl phthalate was added 20 g of 1,2-dihydro-6-methyl-5-(2-methyl-4-thiazolyl)-2-oxo-3-pyridinecarboxylic acid and the resulting dark solution was heated for about 15 minutes and then cooled to about 150° C., treated with decolorizing charcoal and filtered. The filtrate was diluted with 350 ml of n-hexane (no solid precipitated) and then extracted with 300 ml of 3% aqueous sodium hydroxide solution. The aqueous phase was separated and acidified with acetic acid, yielding no precipitate. The acidic solution was concentrated on a rotary evaporator to a volume of about 100 ml and allowed to stand at room temperature overnight. The resulting crystalline yellow solid that had separated was collected, washed with water, dried and then recrystallized from isopropyl alcohol-ether to produce 6.8 g of 6-methyl-5-(2-methyl-4-thiazolyl)-2-(1H)-pyridinone, m.p. 188°–190° C.

C-6. 3-Amino-6-methyl-5-(2-methyl-4-thiazolyl)-2(1H)-pyridinone—To an ice cold stirred solution containing 50 ml of 35% aqueous sodium hydroxide solution and 250 ml of water was added dropwise over a 10 minute period 12 g of bromine and to the resulting solution was added 18.75 g of finely divided 1,2-dihydro-6-methyl-5-(2-methyl-4-thiazolyl)-2-oxo-3-pyridinecarboxamide. The resulting reaction mixture was stirred in an ice bath for 5 hours and then allowed to stand at room temperature overnight. The reaction mixture was acidified with acetic acid and chilled. The tan crystalline solid that separated was collected, washed with water and dried, and then recrystallized from ethanol containing a slight excess of methanesulfonic acid to produce 15.3 g of 3-amino-6-methyl-5-(2-methyl-4-thiazolyl)-2(1H)-pyridinone as its methanesulfonate, m.p. 235°–237° C. This salt was dissolved in water, the solution treated with decolorizing charcoal and filtered. The filtrate made basic with aqueous ammonium hydroxide and then reacidified with acetic acid. The resulting white solid was collected, washed with water and dried at 90° C. to produce 7.1 g of 3-amino-6-methyl-5-(2-methyl-4-thiazolyl)-2(1H)-pyridinone, m.p. 192°–194° C.

Acid-addition salts of 3-amino-6-methyl-5-(2-methyl-4-thiazolyl)-2(1H)-pyridinone are conveniently prepared by adding to a mixture of 1 g of 3-amino-6-methyl-5-(2-methyl-4-thiazolyl)-2(1H)-pyridinone in about 20 ml of methanol the appropriate acid, e.g., hydrochloric acid, methanesulfonic acid, concentrated sulfuric acid, concentrated phosphoric acid, to a pH of about 2 to 3, chilling the mixture after partially evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 3-amino-6-methyl-5-(2-methyl-4-thiazolyl)-2(1H)-pyridinone and the appropriate acid, e.g., lactic acid or hydrochloric acid, to prepare respectively the lactate or hydrochloride salt of 3-amino-6-methyl-5-(2-methyl-4-thiazolyl)-2(1H)-pyridinone in aqueous solution.

Following the procedure described in Example C-1 using in place of 5-(bromoacetyl)-1,2-dihydro-6-methyl-2-oxo-3-pyridinecarbonitrile a molar equivalent quantity of the appropriate 1,2-dihydro-4-$R_2$-5-[$R_3$-CH(Br)CO]-6-$R_1$-2-oxo-3-pyridinecarbonitrile, it is contemplated that the corresponding 1,2-dihydro-4-$R_2$-5-(2-Q'-$R_3$-4-thiazolyl)-6-$R_1$-2-oxo-3-pyridinecarbonitriles of Examples C-7 thru C-11 can be obtained.

C-7. 1,2-Dihydro-6-methyl-5-(2,5-dimethyl-4-thiazolyl)-2-oxo-3-pyridinecarbonitrile, using 5-(2-bromo-n-propanoyl)-1,2-dihydro-6-methyl-2-oxo-3-pyridinecarbonitrile.

C-8. 6-Ethyl-1,2-dihydro-5-(2-methyl-4-thiazolyl)-2-oxo-3-pyridinecarbonitrile, using 5-(bromoacetyl)-6-ethyl-1,2-dihydro-2-oxo-3-pyridinecarbonitrile.

C-9. 1,2-Dihydro-4,6-dimethyl-5-(2-methyl-4-thiazolyl)-2-oxo-3-pyridinecarbonitrile, using 5-(bromoacetyl)-1,2-dihydro-4,6-dimethyl-2-oxo-3-pyridinecarbonitrile.

C-10. 6-Ethyl-1,2-dihydro-5-(2,5-dimethyl-4-thiazolyl)-2-oxo-3-pyridinecarbonitrile, using 5-(2-bromo-n-propanoyl)-6-ethyl-1,2-dihydro-2-oxo-3-pyridinecarbonitrile.

C-11. 5-(5-Ethyl-2-methyl-4-thiazolyl)-1,2-dihydro-2-oxo-6-n-propyl-3-pyridinecarbonitrile, using 5-(2-bromo-n-propanoyl)-1,2-dihydro-2-oxo-6-n-propyl-3-pyridinecarbonitrile.

Following the procedure described in Example C-1 using in place of thioacetamide a molar equivalent quantity of the appropriate alkanamide, it is contemplated that the corresponding 1,2-dihydro-6-methyl-5-(2-alkyl-4-thiazolyl)-2-oxo-3-pyridinecarbonitriles of Examples C-12 thru C-14 can be obtained.

C-12. 5-(2-Ethyl-4-thiazolyl)-1,2-dihydro-6-methyl-2-oxo-3-pyridinecarbonitrile, using n-thiopropanamide.

C-13. 1,2-Dihydro-5-(2-isopropyl-4-thiazolyl)-6-methyl-2-oxo-3-pyridinecarbonitrile, using 2-methyl-n-thiopropanamide.

C-14. 1,2-Dihydro-6-methyl-2-oxo-5-(2-n-propyl-4-thiazolyl)-3-pyridinecarbonitrile, using n-thiobutanamide.

Following the procedure used in Example C-2 using in place of 5-bromoacetyl-1,2-dihydro-6-methyl-2-oxo-3-pyridinecarbonitrile and thiourea molar equivalent quantities respectively of 1,2-dihydro-4-$R_2$-5-[$R_3$-CH(Br)CO]-6-$R_1$-2-oxo-3-pyridinecarbonitrile and N-$R_4$-thiourea, it is contemplated that the following 1,2-dihydro-4-$R_2$-5-[2-($R_4$-NH)-5-$R_3$-4-thiazolyl]-2-oxo-6-$R_1$-3-pyridinecarbonitriles of Examples C-15 thru C-19 can be obtained.

C-15. 1,2-Dihydro-6-methyl-5-(5-methyl-2-methylamino-4-thiazolyl)-2-oxo-3-pyridinecarbonitrile, using 5-(2-bromo-n-propanoyl)-1,2-dihydro-6-methyl-2-oxo-3-pyridinecarbonitrile and N-methylthiourea.

C-16. 5-(2-Amino-4-thiazolyl)-6-ethyl-1,2-dihydro-2-oxo-3-pyridinecarbonitrile, using 5-(bromoacetyl)-6-ethyl-1,2-dihydro-2-oxo-3-pyridinecarbonitrile and thiourea.

C-17. 5-(2-Ethylamino-4-thiazolyl)-1,2-dihydro-4,6-dimethyl-2-oxo-3-pyridinecarbonitrile, using 5-(bromoacetyl)-1,2-dihydro-4,6-dimethyl-2-oxo-3-pyridinecarbonitrile and N-ethylthiourea.

C-18. 6-Ethyl-1,2-dihydro-5-(5-methyl-2-n-propylamino-4-thiazolyl)-2-oxo-3-pyridinecarbonitrile, using 5-(2-bromo-n-propanoyl)-6-ethyl-1,2-dihydro-2-oxo-3-pyridinecarbonitrile and N-(n-propyl)thiourea.

C-19. 5-(2-n-Butylamino-5-ethyl-4-thiazolyl)-1,2-dihydro-6-n-propyl-2-oxo-3-pyridinecarbonitrile, using 5-(2-bromo-n-butanoyl)-1,2-dihydro-2-oxo-6-n-propyl-3-pyridinecarbonitrile and N-(n-butyl)thiourea.

Following the procedures described in Examples C-4 and C-5 using in place of 1,2-dihydro-6-methyl-5-(2-methyl-4-thiazolyl)-2-oxo-3-pyridinecarbonitrile a molar equivalent quantity of the appropriate 1,2-dihydro-4-$R_2$-5-(2-Q'-5-$R_3$-4-thiazolyl)-6-$R_1$-2-oxo-3-pyridinecarbonitrile, it is contemplated that the corresponding 4-$R_2$-5-(2-Q'-$R_3$-4-thiazolyl)-6-$R_1$-2(1H)-pyridinones of Examples C-20 thru C-32 can be obtained.

C-20. 6-Methyl-5-(2,5-dimethyl-4-thiazolyl)-2(1H)-pyridinone, using 5-(2,5-dimethyl-4-thiazolyl)-1,2-dihydro-6-methyl-2-oxo-3-pyridinecarbonitrile.

C-21. 6-Ethyl-5-(2-methyl-4-thiazolyl)-(1H)-pyridinone, using 6-ethyl-1,2-dihydro-5-(2-methyl-4-thiazolyl)-2-oxo-3-pyridinecarbonitrile.

C-22. 4,6-Dimethyl-5-(2-methyl-4-thiazolyl)-(1H)-pyridinone, using 1,2-dihydro-4,6-dimethyl-5-(2-methyl-4-thiazolyl)-2-oxo-3-pyridinecarbonitrile.

C-23. 6-Ethyl-5-(2,5-dimethyl-4-thiazolyl)-2(1H)-pyridinone, using 6-ethyl-1,2-dihydro-5-(2,5-dimethyl-4-thiazolyl)-2-oxo-3-pyridinecarbonitrile.

C-24. 5-(5-Ethyl-2-methyl-4-thiazolyl)-6-n-propyl-2(1H)-pyridinone, using 5-(5-ethyl-2-methyl-4-thiazolyl)-1,2-dihydro-2-oxo-6-n-propyl-3-pyridinecarbonitrile.

C-25. 5-(2-Ethyl-4-thiazolyl)-6-methyl-2(1H)-pyridinone, using 5-(2-ethyl-4-thiazolyl)-1,2-dihydro-6-methyl-2-oxo-3-pyridinecarbonitrile.

C-26. 5-(2-Isopropyl-4-thiazolyl)-6-methyl-2(1H)-pyridinone, using 1,2-dihydro-5-(2-isopropyl-4-thiazolyl)-6-methyl-2-oxo-3-pyridinecarbonitrile.

C-27. 6-Methyl-5-(2-n-propyl-4-thiazolyl)-2(1H)-pyridinone, using 1,2-dihydro-6-methyl-2-oxo-5-(2-n-propyl-4-thiazolyl)-3-pyridinecarbontrile.

C-28. 6-Methyl-5-(5-methyl-2-methylamino-4-thiazolyl)-2(1H)-pyridinone, using 5-(5-methyl-2-methylamino-4-thiazolyl)-1,2-dihydro-6-methyl-2-oxo-3-pyridinecarbonitrile.

C-29. 5-(2-Amino-4-thiazolyl)-6-ethyl-2(1H)-pyridinone, using 5-(2-amino-4-thiazolyl)-6-ethyl-1,2-dihydro-2-oxo-3-pyridinecarbonitrile.

C-30. 5-(2-Ethylamino-4-thiazolyl)-4,6-dimethyl-2(1H)-pyridinone, using 5-(2-ethylamino-4-thiazolyl)-1,2-dihydro-4,6-dimethyl-2-oxo-3-pyridinecarbonitrile.

C-31. 6-Ethyl-5-(5-methyl-2-n-propylamino-4-thiazolyl)-2(1H)-pyridinone, using 5-(5-methyl-2-n-propylamino-4-thiazolyl)-6-ethyl-1,2-dihydro-2-oxo-3-pyridinecarbonitrile.

C-32. 5-(2-n-Butylamino-5-ethyl-4-thiazolyl-6-n-propyl-2(1H)-pyridinone, using 5-(2-n-butylamino-5-ethyl-4-thiazolyl)-1,2-dihydro-2-oxo-6-n-propyl-3-pyridinecarbonitrile.

Following the procedures described in Examples C-3 and C-6 using in place of 1,2-dihydro-6-methyl-5-(2-methyl-4-thiazolyl)-2-oxo-3-pyridinecarbonitrile a molar equivalent quantity of the appropriate 1,2-dihydro-4-$R_4$-5-(2-$Q'$-5-$R_3$-4-thiazolyl)-6-$R_1$-2-oxo-3-pyridinecarbonitrile, it is contemplated that the corresponding 3-amino-4-$R_2$-5-(2-$Q'$-$R_3$-4-thiazolyl)-6-$R_1$-2(1H)-pyridinones of Examples C-33 thru C-45 can be obtained.

C-33. 3-Amino-6-methyl-5-(2,5-dimethyl-4-thiazolyl)-2(1H)-pyridinone, using 1,2-dihydro-6-methyl-5-(2,5-dimethyl-4-thiazolyl)-2-oxo-3-pyridinecarbonitrile.

C-34. 3-Amino-6-ethyl-5-(2-methyl-4-thiazolyl)-2(1H)-pyridinone, using 6-ethyl-1,2-dihydro-5-(2-methyl-4-thiazolyl)-2-oxo-3-pyridinecarbonitrile.

C-35. 3-Amino-4,6-dimethyl-5-(2-methyl-4-thiazolyl)-(1H)-pyridinone, using 1,2-dihydro-4,6-dimethyl-5-(2-methyl-4-thiazolyl)-2-oxo-3-pyridinecarbonitrile.

C-36. 3-Amino-6-ethyl-5-(2,5-dimethyl-4-thiazolyl)-2(1H)-pyridinone, using 6-ethyl-1,2-dihydro-5-(2,5-dimethyl-2-thiazolyl)-2-oxo-3-pyridinecarbonitrile.

C-37. 5-(5-Ethyl-2-methyl-4-thiazolyl)-6-n-propyl-2(1H)-pyridinone, using 5-(5-ethyl-2-methyl-4-thiazolyl)-1,2-dihydro-2-oxo-6-n-propyl-3-pyridinecarbonitrile.

C-38. 3-Amino-5-(2-ethyl-4-thiazolyl)-6-methyl-(1H)-pyridinone, using 5-(2-ethyl-4-thiazolyl)-1,2-dihydro-6-methyl-2-oxo-3-pyridinecarbonitrile.

C-39. 3-Amino-5-(2-isopropyl-4-thiazolyl)-6-methyl-2(1H)-pyridinone, using 1,2-dihydro-5-(2-isopropyl-4-thiazolyl)-6-methyl-2-oxo-3-pyridinecarbonitrile.

C-40. 3-Amino-6-methyl-5-(2-n-propyl-4-thiazolyl)-2(1H)-pyridinone, using 1,2-dihydro-6-methyl-2-oxo-5-(2-n-propyl-4-thiazolyl)-3-pyridinecarbonitrile.

C-41. 3-Amino-6-methyl-5-(5-methyl-2-methylamino-4-thiazolyl)-2(1H)-pyridinone, using 1,2-dihydro-6-methyl-5-(5-methyl-2-methylamino-4-thiazolyl)-2-oxo-3-pyridinecarbonitrile.

C-42. 3-Amino-5-(2-amino-4-thiazolyl)-6-ethyl-(1H)-pyridinone, using 5-(2-amino-4-thiazolyl)-6-ethyl-1,2-dihydro-2-oxo-3-pyridinecarbonitrile.

C-43. 3-Amino-5-(2-ethylamino-4-thiazolyl)-1,2-dihydro-4,6-dimethyl-2(1H)-pyridinone, using 5-(2-ethylamino-4-thiazolyl)-1,2-dihydro-4,6-dimethyl-2-oxo-3-pyridinecarbonitrile.

C-44. 3-Amino-6-ethyl-1,2-dihyro-5-(5-methyl-2-n-propylamino-4-thiazolyl)-2(1H)-pyridinone, using 6-ethyl-1,2-dihydro-5-(5-methyl-2-n-propylamino-4-thiazolyl)-2-oxo-3-pyridinecarbonitrile.

C-45. 3-Amino-5-(2-n-butylamino-5-ethyl-4-thiazolyl)-6-n-propyl-2(1H)-pyridinone, using 5-(2-n-butylamino-5-ethyl-4-thiazolyl)-1,2-dihydro-2-oxo-6-n-propyl-3-pyridinecarbonitrile.

The utility of the compounds of formula I where Q is amino, cyano or hydrogen or their pharmaceutically acceptable acid-addition salts where Q or Q' is amino or Q' is $R_4NH$ as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat or guinea pig atria and papillary muscle procedure, the compounds of the invention or said salts thereof at doses of 3, 10, 30, and/or 100 µg/ml., were found to cause significant increases, that is, greater than 25% (cat) or 30% (g. pig) in papillary muscle force and significant increases, that is, greater than 25% (cat) or 30% (g. pig) in right atrial force, while causing a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, illustrative guinea pig papillary muscle and right atrial force increases for compounds of the invention are: 69% and 57% at 10 µg./ml and 100% and 113% at 30 µg/ml for the compound of Example C-1; 68% and 45% at 10 µg/ml and 61% and 45% at 30 µg/ml for the compound of Example C-2; 51% and 40% at 30 µg/ml and 63% and 89% at 100 µg/ml for the compound of Example C-5; and, 47% and 53% at 30 µg/ml and 60% and 130% at 100 µg/ml for the compound of Example C-6.

When tested by said anesthetized dog procedure, the compounds of the invention or said salts thereof at doses of 0.3, 1.0, 3.0 and/or 10 mg./kg. administered intravenously were found to cause significant increases, that is, 25% or greater, in cardiac contractile force or cardiac contractility with lower changes in heart rate and blood pressure. For example, the compound of Example C-1 was found to cause respective increases of 36%, 111% and 58% in contractile force at doses of 0.3, 1.0 and 3.0 mg/kg; and, the compound of Example C-6 was found to cause respective increases of 32%, 71% and 93% at doses of 1.0, 3.0 and 10.0 mg/kg.

The present invention includes within its scope a cardiotonic composition for increasing cardiac contractility, said composition comprising a pharmaceutically acceptable carrier and, as the active component thereof, a cardiotonically effective amount of the compound of formula I where Q is amino, cyano or hydrogen or said salt thereof. The invention also includes within its scope the method for increasing cardiac contractility in a patient requiring such treatment which comprises administering to such patient said cardiotonic composition providing a cardiotonically effective amount of the compound of formula I or said salt thereof. In clinical practice said compound will normally be administered orally or parenterally in a wide variety of dosage forms.

Solid compositions for oral admininstration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such a magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. 3-Q-4-$R_2$-5-(2-Q'-5-$R_3$-4-thiazolyl)-6-$R_1$-2(1H)-pyridinone having the formula

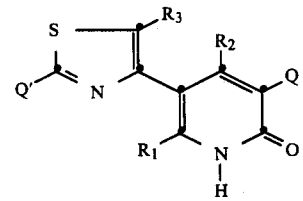

where $R_1$ is alkyl having one to four carbon atoms, $R_2$ is hydrogen or methyl, $R_3$ is hydrogen or alkyl having from one to three carbon atoms, Q is cyano and Q' is alkyl having from one to four carbon atoms, amino or $R_4$NH where $R_4$ is alkyl having one to four carbon atoms; or an acid-addition salt thereof where Q' is amino or $R_4$NH.

2. A compound according to claim 1 where $R_1$ is methyl or ethyl, and $R_2$ and $R_3$ are each hydrogen.

3. 1,2-Dihydro-6-methyl-5-(2-methyl-4-thiazolyl)-2-oxo-3-pyridinecarbonitrile according to claim 2.

4. A cardiotonic composition for increasing cardiac contracility, said composition comprising a pharmaceutically acceptable carrier and, as the active component thereof, a cardiotonically effective amount of 3-Q-4-$R_2$-5-(2-Q'-5-$R_3$-4-thiazolyl)-6-$R_1$-2(1H)-pYridinone of claim 1 where $R_1$, $R_2$, $R_3$ and Q' are defined as in claim 1 and Q is cyano; or pharmaceutically acceptable acid-addition salt thereof where Q' is amino or $R_4$NH.

5. A composition according to claim 4 where $R_1$ is methyl or ethyl and $R_3$ is hydrogen.

6. A composition according to claim 5 where the active component is 1,2-dihydro-6-methyl-5-(2-methyl-4-thiazolyl)-2-oxo-3-pyridinecarbonitrile.

7. The method for increasing cardiac contractility in a patient requiring such treatment which comprises administering orally or parenterally in a solid or liquid dosage form to such patient an effective amount of a cardiotonic composition according to claim 4.

8. The method according to claim 7 where $R_1$ is methyl or ethyl and $R_3$ is hydrogen.

9. The method according to claim 8 where the active component is 1,2-dihydro-6-methyl-5-(2-methyl-4-thiazolyl)-2-oxo-3-pyridinecarbonitrile.

* * * * *

UNITED STATES PATENT AND TRADEMARK OFFICE
CERTIFICATE OF CORRECTION

PATENT NO. : 4,469,699

DATED : September 4, 1984

INVENTOR(S) : G.Y. Lesher and B. Singh

It is certified that error appears in the above-identified patent and that said Letters Patent is hereby corrected as shown below:

Column 3, line 5, "5-2(2" should read -- 5-(2 --.

Column 16, line 40, "pYridinone" should read -- pyridinone --.

Signed and Sealed this

Twentieth Day of August 1985

[SEAL]

Attest:

DONALD J. QUIGG

Attesting Officer     Acting Commissioner of Patents and Trademarks